United States Patent [19]
DeLuca et al.

[11] Patent Number: 4,461,618
[45] Date of Patent: Jul. 24, 1984

[54] PROCESS FOR PRODUCING A DENTAL RESTORATION

[75] Inventors: Robert D. DeLuca, Pennington; Robin M. F. Jones, Titusville, both of N.J.

[73] Assignee: Johnson & Johnson Dental Products Company, East Windsor, N.J.

[21] Appl. No.: 440,231

[22] Filed: Nov. 10, 1982

Related U.S. Application Data

[63] Continuation-in-part of Ser. No. 342,258, Jan. 25, 1982, abandoned.

[51] Int. Cl.$^3$ .............................................. A61K 6/08
[52] U.S. Cl. ....................................... 433/200; 427/2; 433/201; 433/206; 433/207; 433/208; 433/222; 433/223
[58] Field of Search ............... 433/200, 206, 207, 208, 433/215, 217, 201, 222, 223; 427/2

[56] References Cited

U.S. PATENT DOCUMENTS

| | | | |
|---|---|---|---|
| 1,736,053 | 11/1929 | Rohn | 75/171 |
| 2,134,423 | 10/1938 | Touceda | 75/171 |
| 2,156,757 | 5/1939 | Grossman | 75/171 |
| 2,162,252 | 6/1939 | Grossman | 75/171 |
| 2,631,095 | 3/1953 | Griffiths et al. | 75/171 |
| 3,121,629 | 2/1964 | Mann | 75/171 |
| 3,464,817 | 9/1969 | Griffiths | 75/171 |
| 3,544,315 | 12/1970 | Asgar | 75/171 |
| 3,685,115 | 8/1972 | Scott | 29/160.6 |
| 3,716,418 | 2/1973 | Kochavi | 75/171 |
| 3,761,728 | 9/1973 | Kochavi | 29/160.6 |
| 3,834,024 | 9/1974 | Kochavi | 32/8 |
| 4,129,944 | 12/1978 | Sung et al. | 32/8 |

FOREIGN PATENT DOCUMENTS 1529267 10/1978 United Kingdom .

Primary Examiner—Lorenzo B. Hayes
Attorney, Agent, or Firm—Charles J. Metz

[57] ABSTRACT

A process for producing a dental restoration wherein a bonding agent is disclosed for bonding dental porcelain to a nickel-containing metal core. The bonding agent is aluminum powder and an inert organic liquid carrier.

6 Claims, No Drawings

PROCESS FOR PRODUCING A DENTAL RESTORATION

This application is a continuation-in-part of our co-pending application Ser. No. 342,258, filed Jan. 25, 1982, now abandoned.

The invention relates to a dental bonding agent composed of aluminum powder in an inert liquid organic carrier, to a process wherein said bonding agent is used to bond dental porcelain to a metal core, and to the dental restorations produced by said process.

BACKGROUND OF THE INVENTION

Dental restorations generally comprise a metal core or framework to which porcelain is bonded on the visible surfaces for esthetic reasons. For many years gold has been the basic structural metal for preparing the core or framework. However, because of the high cost of gold, many attempts have been made to devise non-precious metal alloys which could be used in place of gold. Such compositions are illustrated, for example, by U.S. Pat. Nos. 1,736,053; 2,089,587; 2,156,757; 2,134,423; 2,162,252; 2,631,095; 3,121,629; 3,464,817; 3,544,315; 3,685,115; 3,716,418; 3,761,728; and 3,834,024; and in standard dental literature such as Skinner and Phillips, "THE SCIENCE OF DENTAL MATERIALS," p. 582, Sixth edition, W. B. Saunders Company, Philadelphia and London, 1967 and Morrey and Nelson, "DENTAL SCIENCES HANDBOOK," p. 168, American Dental Association and National Institute of Dental Research, U.S. Government Printing Office, Washington, D.C., 1970. Suitable alloys are typically nickel or cobalt-based alloys, particularly, nickel-chromium alloys.

This invention is directed to a bonding agent and to a method for bonding dental porcelain to a nickel-containing non-precious metal alloy framework. When dental porcelain is bonded to the metal framework using the bonding agents of this invention, a strong bond is formed which is able to resist separation of the porcelain under far greater stresses than in the absence of bonding agent. Moreover, the bonding agents of this invention can be used under less critical conditions than prior, similar bonding agents.

BRIEF SUMMARY OF THE INVENTION

The bonding agent of this invention is aluminum powder plus an inert liquid organic carrier. The method of the invention comprises: (a) applying to a surface of a cleaned nickel-containing metal core a coating of the bonding agent of the invention; (b) baking the coated metal core in a substantially inert atmosphere to a temperature and for a period of time sufficient to form an aluminide layer on the surface of said metal core; (c) cleaning the coated and baked surface; and (d) applying porcelain to the baked and cleaned surface and firing.

The article of the invention is a dental restoration comprising a metal core with a porcelain coating wherein the porcelain is bonded to the metal core with the bonding agent of the invention.

THE PRIOR ART

Schmick, in U.S. Pat. No. 2,996,419, discloses a bonding agent for joining glass to glass which consists of powdered aluminum and a non-volatile silicone resin that decomposes during firing to leave a residue of silica. British Pat. No. 1,529,267 (Jan. 24, 1979) discloses a bonding agent for joining porcelain to a metal core for making dental restorations, wherein the bonding agent comprises powdered aluminum, powdered glass, and a volatile liquid silicone oil carrier. The bonding agent described in the British patent was marketed commercially substantially as described in the patent, and then in an improved version wherein the silicone oil carrier was replaced by propylene glycol.

DETAILED DESCRIPTION OF THE INVENTION

The aluminum is employed in the form of a finely divided powder which preferably has an average particle diameter below about 25 microns. While the exact particle size is not critical, most (e.g., at least about 90 percent) of the particles should be below 200 mesh in order for the bonding agent to have acceptable handling characteristics.

The aluminum powder is employed in an inert liquid organic carrier. Illustrative organic carriers include propylene glycol, glycerol, esters, ketones, liquid hydrocarbons, and other organic materials that will volatilize and will not react with either the aluminum or the metal core so as to interfere with the aluminiding reaction.

The organic liquid is used in appropriate proportions so that the bonding agent can be applied by brushing, spraying or dipping. Exact proportions can be determined by routine experimentation, but will usually be found a liquid:powder weight ratio within the range of from about 1:2 to 5:1.

The bonding agent composition can be prepared by simply mixing the carrier with the aluminum powder to form a slurry.

The powder and carrier may be mixed just before use, or they may be pre-mixed.

The metal core is thoroughly cleaned before the bonding agent is applied. Cleaning can be by conventional procedures such as scrubbing with abrasive, brushing, ultrasonic cleaning in water, or the like. The bonding agent is then applied in a thin coat over the metal, using a brush or a spatula, spraying, or dipping, to yield a coating about 1 to 2 mils thick.

The coated metal core is then fired.

Typical firing conditions are the following:

Insert the coated metal core in a furnace at about 1200° F., then either evacuate the furnace or fill it with an inert atmosphere such aas argon, nitrogen, or the like. Evacuation is preferred since most dental laboratories are equipped with a vacuum furnace. Then increase the temperature at the rate of about 100° F. per minute to a maximum temperature of about 1550° F. to about 1850° F. When the maximum temperature is reached, the article is cooled by admitting ambient air into the furnace and then cooling in air to room temperature.

During the firing, the aluminum powder reacts with nickel in the metal core to form nickel aluminide.

After the coated metal core has been fired, it is preferably ultrasonically cleaned in water to remove non-adhering materials. Care should be taken in this step to remove all non-adhering materials.

The porcelain is applied to the bonding agent coated metal surface in any appropriate manner normally employed to coat metal surfaces in the absence of a bonding agent. Preferred methods are painting on with a brush or coating with a spatula. After application of the porcelain, the porcelain is fired at temperatures appropriate for the particular porcelain and metal employed.

Thus, it may be carried out at any appropriate temperature range within the broader limits of from about 1600° F. to about 2000° F. Thereafter, additional coatings of porcelain may be applied and fired in a conventional manner to complete the production of the dental restoration in which a bond is formed between the metal and porcelain which is resistant to separation on application of mechanical stresses.

The bonding agent compositions of this invention are adapted to be employed with nickel-containing metal alloys and porcelains which are suitable for use together in the absence of a bonding agent.

Metal alloys for which the bonding agent compositions of the invention are useful are the nickel based alloys, particularly the nickel-chromium alloys. Representative alloys are found in the aforementioned patents and dental literature on non-precious metal alloys. Other nickel-containing alloys with which the bonding agent composition may be employed are available under various trade names. Still other alloys with which the bonding agent compositions are usefully employed are disclosed in U.S. Pat. No. 4,129,944, and in published European Patent Application No. 5013, published Oct. 31, 1979.

The porcelain which is to be bonded to the dental alloy may be any porcelain appropriate to be employed with the alloy chosen. By "porcelain" is meant dental porcelain as known in the art and embraces dental glasses. They generally contain silicon oxide, aluminum oxide, potassium oxide, sodium oxide, and minor amounts of other oxides. Normally, the porcelain covering which is first applied to the metal is an opaque porcelain. An opaque porcelain reduces the tendency of the metal to be seen through the final coating. Opaque porcelains are available commercially and include in the oxide composition either zirconium oxide, tin oxide, titanium oxide, or zirconium silicate as an opaquing agent. The opaque porcelain is normally coated with a relatively thick layer or layers of body porcelain followed usually by a final layer or coating at the tips of incisal porcelain. The body porcelain is available commercially as gingival or body porcelain (sometimes called dentine) and may have a small amount of opaquing agent, and incisal porcelain is usually of similar composition as body porcelain without opaquing agent. In all coatings subsequent to the first coating, porcelain is bonded to porcelain. In the first coating, porcelain is bonded to metal and the problems to be solved by the bonding agent composition of the present invention are with the porcelain-to-metal relationship. Thus, it is solely the porcelain which is to be bonded to metal which is of concern in the practice of the present invention. Since under present practice, the porcelain which is bonded to metal is that understood in the art as opaque porcelain, the porcelains which are to be bonded to metal by the bonding agent compositions usually are opaque porcelains, although not limited thereto.

The selection of the procelain in terms of exact composition is dependent to a greater degree on the metal alloy substrate which is to be faced with the porcelain than on the bonding agent. For the bonding agent to have the advantageous properties provided by the invention, it is expected that the selection of the procelain be appropiate for the metal alloy core or substrate employed. Thus, the thermal expansion properties of porcelain should be compatible or reasonably matched with that of the alloy. It is recognized that a meaningful single coefficient of expansion is not obtainable for porcelain as it is for metal over the broad temperature range of about 25° to 600° C. and that coefficients of expansion values are valid only for a narrow range of temperatures. Frequently, therefore, after preliminary determination of the coefficients of expansion, empirical methods are employed for the selection of the porcelain to be employed with the particular alloy. The method of selection of porcelain for use with a particular alloy is not part of the present invention, but when a reasonably "matched" porcelain and metal alloy are to be bonded together, the use of the bonding agent of this invention greatly enhances the bonding properties.

The following examples illustrate the practice of the invention:

EXAMPLE 1

A major advantage of the bonding agent of this invention is that the procedure for using it is relatively non-critical. Therefore, excellent results can be obtained more readily in the dental laboratory over a wider variety of conditions. The experiments discussed in this Example 1 demonstrate this advantage.

EXPERIMENTAL PROCEDURE

A. Alloy Specimen

CERAMALLOY II* flags (3 cm long×1 cm wide×0.5 mm thick) were investment cast and a 1 cm area in the center of the flag was roughened using a diamond handpiece in preparation for bonding agent application. All flags were ultrasonically cleaned in distilled water.
*Trademark of Johnson & Johnson—An alloy containing Nickel, Chromium, Silicon, Molybdenum, and Boron.

B. Aluminum Powder

Various grades of Alcoa Powder were tested for use as a bonding agent and Alcoa 123 and Alcoa 101 were selected on the basis of particle size and ease of application. The specification for these powders are given in Table I.

C. Application

Different thickness of bonding agent was accomplished by varying the liquid to powder ratio in the following manner:

(1) Thin Coat

Enough propylene glycol was mixed with aluminum powder so that the mix will drip easily from the spatula. A quantity just enough to cover the metal was brushed on.

(2) Medium Coat

Powder and propylene glycol was mixed so that the mix gave a good paintable consistency and clung moderately to the spatula. An even coat was applied over the metal surface.

(3) Thick Coat

Powder and propylene glycol were mixed so that the material clung strongly to the spatula. An even coat was applied over the metal surface.

D. Firing of Bonding Agent

After the application of the bonding agent, the flags were dried on the furnace door and inserted in the furnace at 1200° F., the furnace was evacuated and the furnace temperature was raised to 1550° F.; 1650° F.;

1750° F.; or 1850° F. at a rate of 100° F./min. Samples were removed from the furnace and bench cooled to room temperature.

E. Surface Preparation After Firing the Bonding Agent

One set of flags were scrubbed with a medium Robinson Brush using a dental handpiece. This was followed by a 10 minute ultrasonic cleaning in tap water.

Another set of flags were only ultrasonically cleaned in tap water for 10 minutes.

F. Porcelain Application

A standard opaque porcelain was applied and fired at 1200° F.-1700° F. under vacuum, 1700° F.-1850° F. in air, and bench cooled.

G. Porcelain/Metal Bond Testing

Standard flexure adhesion test was used to determine the porcelain bonding characteristics. The test is described by W. J. O'Brien in a chapter entitled "Cohesive Plateau Theory of Porcelain-Alloy Bonding", in "Dental" "Porcelain", edited by Yamada et al., University of Southern California (1977).

EXPERIMENTAL RESULTS AND DISCUSSION

The effects of various factors on the porcelain bonding characteristics were:

A. Effect of Mixing and Application Variations

The effect of mixing and application of powder (Alcoa 123) and liquid (propylene glycol) components of the bonding agent affect the thickness of the bonding agent coating during application. The effect of thin, medium and thick coating on the percentage porcelain retention at various firing temperatures is summarized in Table II. These results show very little variation in the percentage porcelain retention with the change in bonding agent thickness. Greater than 95% retention was obtained in all the cases.

B. Effect of Firing Temperature Variation

Table III summarizes the flexure adhesion data to show the effect of bonding agent firing temperature on the percentage porcelain retention. These results show very little variation in the percentage porcelain retention data with firing temperature between 1550° F.-1850° 1 F.

C. Effect of Surface Preparation After Bonding Agent Firing

The surface of the metal flag after bonding agent firing was cleaned using Robinson Brush and ultrasonic or ultrasonic alone. The effect of this variable on percentage porcelain retention can be seen from the data in Table III. There is no noticeable difference in the percentage porcelain retention between specimen cleaned using Robinson Brush and ultrasonic cleaning or ultrasonic cleaning alone.

Before Bonding Agent Application

The effect of metal surface preparation before applying the bonding agent on the percentage porcelain retention is given in Table IV. The standard procedure for the preparation of the metal surface is to roughen it with a diamond instrument before applying the bonding agent. This was compared with metal surface which was grit-blasted and polished (using a rubber wheel). A medium coating of bonding agent (Alcoa 123 and propylene glycol) was applied and fired to 1550° F. The surface was ultrasonically cleaned before applying the opaque porcelain. These results show comparable values, thus indicating that the surface roughening is not necessary in this type of bonding because of the chemical nature of bonding. Metallographic examination of the interface shows superior bonding in case of polished (rubber wheeled) metal surface.

D. Effect of Aluminum Powder Particle Size

Alcoa 101 Powder is slightly coarser than Alcoa 123 Powder (See Table I). Therefore, in order to see any changes in percentage porcelain retention, Alcoa 101 was compared with Alcoa 123, using thin and medium coats, fired to 1550° F. The results are given in Table V.

These results show excellent porcelain retention using Alcoa 101. Therefore, minor variations in aluminum powder particle size do not affect the percent porcelain retention.

E. Other Results

Table VI summarizes the results of the flexure adhesion test to confirm the effects of the improved bonding agent:

1. To see if the oxidation of CERAMALLOY II* at 1550° F. affects the percentage porcelain retention. Opaque porcelain was applied directly on the oxide. The poor results show the variability of oxide adhesion to the metal surface.
2. To see the effect of full porcelain firing cycle on the bonding agent, specimens after the bonding agent firing were given simulated thermal cycles of gingival and incisal porcelain firing. The excellent results show no detrimental effect of thermal cycling on the effectiveness of this bonding agent.

TABLE I

TYPICAL PROPERTIES OF REGULAR ATOMIZED ALUMINUM POWDERS

| Grade | | Chemical Analysis % | | | Screen Analysis % (U.S. Standard Sieve) | | | | Density | | Average[1] Particle Diameter Microns | Typical Particle Size Distribution[2] | | Surface Area++ $m^2gm$ |
|---|---|---|---|---|---|---|---|---|---|---|---|---|---|---|
| | | Typical Range | Limits Min. | Max. | Mesh | Typical Range | Shipment Min. | Max. | Apparent g/cc (lb./ft.$^3$) | Tapped g/cc (lb. ft.$^3$) | | Wt. %[3] | Microns | |
| 123 | Al | 99.7 | | | +200 | 0-Trace | | 0.2 | 1.1 (69) | 1.4 (88) | 15-19 | 90 | 49 | .20-.30 |
| | | | | | | | | | | | | 80 | 42 | |
| | Fe | 0.18 | | 0.25 | -200 +325 | 1-10 | | | | | | 50 20 | 29 18 | |
| | Si | 0.12 | | 0.15 | -325 | 90-99+ | 90.0 | | | | | 0 | 4 | |
| 101 | Al | 99.7 | | | +100 | 0-Trace | | 0.2 | 1.1 (69) | 1.5 (94) | 17-24 | 90 | 70 | .15-.20 |
| | | | | | | | | | | | | 80 | 55 | |
| | Fe | 0.18 | | 0.25 | -100 +200 | 0-5 | | | | | | 50 20 | 34 20 | |
| | | | | | -200 | 10-25 | | | | | | 0 | 4 | |

TABLE I-continued

TYPICAL PROPERTIES OF REGULAR ATOMIZED ALUMINUM POWDERS

| Grade | Chemical Analysis % Typical Range | Chemical Analysis % Limits Min. | Chemical Analysis % Limits Max. | Screen Analysis % (U.S. Standard Sieve) Mesh | Screen Analysis % (U.S. Standard Sieve) Typical Range | Screen Analysis % (U.S. Standard Sieve) Shipment Min. | Screen Analysis % (U.S. Standard Sieve) Shipment Max. | Density Apparent g/cc (lb./ft.$^3$) | Density Tapped g/cc (lb. ft.$^3$) | Average[1] Particle Diameter Microns | Typical Particle Size Distribution[2] Wt. %[3] | Typical Particle Size Distribution[2] Microns | Surface Area++ m$^2$gm |
|---|---|---|---|---|---|---|---|---|---|---|---|---|---|
| Si | 0.12 | | 0.15 | +325 −325 | 75-90 | 75.0 | 9.0 | | | | | | |

NOTE:
The above metal analysis excluded 0.6% Al$_2$O$_3$ which exists on the surface of the particle.
[1] Fisher Sub-Sieve Sizer
[2] Sharples Micromerograph
[3] Weight % Undersize

TABLE II

EFFECT OF BONDING AGENT APPLICATION

| BONDING AGENT VARIABLES APPLI- CATION | BONDING AGENT VARIABLES FIRING TEMP. | BONDING AGENT VARIABLES CLEANING AFTER FIRING | % PORCELAIN RETENTION (Max. and Min. of 10 SAMPLES) | AVERAGE |
|---|---|---|---|---|
| | 1550° F. | Thin R.B. & U.S.[4] | All 100 | 100.0 |
| | | U.S. | All 100 | 100.0 |
| | | Medium R.B. & U.S. | 95-100 | 98.7 |
| | | U.S. | 91-100 | 96.7 |
| | | Thick R.B. & U.S. | 95-100 | 98.1 |
| | | U.S. | 95-100 | 98.7 |
| | 1650° F. | Thin R.B. & U.S. | 94-100 | 98.3 |
| | | U.S. | All 100 | 100.0 |
| | | Medium R.B. & U.S. | 94-100 | 98.2 |
| | | U.S. | All 100 | 100.0 |
| | | Thick R.B. & U.S. | 91-100 | 98.7 |
| | | U.S. | 96-100 | 97.8 |
| | 1750° F. | Thin R.B. & U.S. | 97-100 | 98.7 |
| | | U.S. | 97-100 | 99.7 |
| | | Medium R.B. & U.S. | 97-100 | 99.0 |
| | | U.S. | 97-100 | 98.8 |
| | | Thick R.B. & U.S. | 91-100 | 95.1 |
| | | U.S. | 94-100 | 98.4 |
| | 1850° F. | Thin R.B. & U.S. | All 100 | 100.0 |
| | | U.S. | 96-100 | 97.9 |
| | | Medium R.B. & U.S. | 95-100 | 99.5 |
| | | U.S. | 88-100 | 95.1 |
| | | Thick R.B. & U.S. | 97-100 | 99.0 |
| | | U.S. | 98-100 | 99.1 |

[4] R.B. & U.S.—Robinson Brush & Ultrasonic
U.S.—Ultrasonic

TABLE III

EFFECT OF BONDING AGENT APPLICATION

| BONDING AGENT VARIABLES APPLICATION | FIRING TEMP. | CLEANING AFTER FIRING | % PORCELAIN RETENTION (Max. and Min. of 10 SAMPLES) | AVERAGE |
|---|---|---|---|---|
| Thin | 1550° F. | R.B. & U.S. | All 100 | 100.0 |
| | | U.S. | All 100 | 100.0 |
| | 1650° F. | R.B. & U.S. | 94-100 | 98.3 |
| | | U.S. | All 100 | 100.0 |
| | 1750° F. | R.B. & U.S. | 97-100 | 99.7 |
| | | U.S. | 97-100 | 99.0 |
| | 1850° F. | R.B. & U.S. | All 100 | 100.0 |
| | | U.S. | 96-100 | 97.9 |
| Medium | 1550° F. | R.B. & U.S. | 95-100 | 98.7 |
| | | U.S. | 91-100 | 96.7 |
| | 1650° F. | R.B. & U.S. | 94-100 | 98.2 |
| | | U.S. | All 100 | 100.0 |
| | 1750° F. | R.B. & U.S. | 97-100 | 99.1 |
| | | U.S. | 97-100 | 98.8 |
| | 1850° F. | R.B. & U.S. | 95-100 | 99.5 |
| | | U.S. | 88-100 | 95.1 |
| Thick | 1550° F. | R.B. & U.S. | 95-100 | 98.1 |
| | | U.S. | 95-100 | 98.7 |
| | 1650° F. | R.B. & U.S. | 91-100 | 98.7 |
| | | U.S. | 96-100 | 97.8 |
| | 1750° F. | R.B. & U.S. | 91-100 | 95.1 |
| | | U.S. | 94-100 | 98.4 |
| | 1850° F. | R.B. & U.S. | 97-100 | 99.0 |
| | | U.S. | 98-100 | 99.1 |

TABLE IV

EFFECT OF METAL SURFACE PREPARATION

| METAL SURFACE PREPARATION | % PORCELAIN RETENTION (10 SAMPLES) | AVERAGE |
|---|---|---|
| Ground | 91-100 | 96.7 |
| Grit Blasted | 92-100 | 97.4 |
| Polished | 94-100 | 98.5 |

TABLE V

EFFECT OF ALUMINUM POWDER SIZE
ALCOA 101 POWDER

| BONDING AGENT VARIABLES FIRING TEMP. | APPLICATION | CLEANING AFTER FIRING | % PORCELAIN RETENTION (Max. and Min. of 10 SAMPLES) | AVERAGE |
|---|---|---|---|---|
| 1550° F. | Thin | R.B. & U.S. | All 100 | 100.0 |
| | | U.S. | 95-98 | 96.5 |
| | Medium | R.B. & U.S. | 93-100 | 97.2 |
| | | U.S. | 94-100 | 98.2 |

TABLE VI

OTHER RESULTS

| TEST CONDITIONS | % PORCELAIN RETENTION (10 SAMPLES) | AVERAGE |
|---|---|---|
| 1. CERAMALLOY II* oxidized at 1200–1550° F. and P.O.P. applied directly onto the oxide. | 25-100 | 71.3 |
| 2. CERAMALLOY II* improved bonding agent (medium coat, fired to 1550° F., ultrasonically cleaned) applying P.O.P. and giving a simulated full porcelain firing treatment. | All 100 | 100.0 |

The foregoing Example illustrates the fact that the bonding agent of the invention can be employed over a wide range of conditions. In contrast, the prior commercial bonding agent composed of aluminum powder, glass powder, and a carrier such as propylene glycol, had to be used under much more critical conditions. For instance, the minimum firing temperature was about 1750° F., and the best firing temperature was even higher, e.g., about 1900° F. Thus, when the coated metal core was exposed to air after firing, oxidation of exposed metal core occurred. The resulting oxide layer had to be removed because it was unesthetic and rough. The thickness of the coating was also quite critical in that the range of thicknesses that had to be used to obtain adequate adhesion was quite small. And finally, a stiff brush had to be used to clean the fired coated metal in order to remove inadequately adhered and excess bonding agent.

If desired, a thixotropic agent (i.e., a material to impart thixotropy) can be added to the bonding agent of the invention. Such materials as colloidal silica, finely divided magnesium aluminum silicate, finely divided alumina, or other similar materials, can be added in small amounts (i.e., less than 1 weight percent and preferably less than ½ weight percent, based on weight of aluminum) to enhance the adhesion of the unfired bonding agent. At these low proportions, little, if any, effect on other properties is noted. A small amount of water can be used with the thixotropic agent to enhance its effect.

What is claimed is:

1. Process for producing a dental restoration which comprises:
    (a) applying to a surface of a cleaned nickel-containing metal core a coating of a composition that consists of powdered aluminum and an inert volatile organic liquid carrier;
    (b) baking the coated metal core in a substantially inert atmosphere to a temperature and for a period of time sufficient to form a continuous layer consisting of nickel aluminide on said surface;
    (c) cleaning the coated and based surface; and
    (d) applying porcelain to the baked and cleaned surface and firing.

2. The process of claim 1 wherein said carrier is propylene glycol.

3. The process of claim 1 wherein said inert atmosphere is a vacuum.

4. The process of claim 2 wherein said inert atmosphere is a vacuum.

5. A dental restoration which comprises a nickel-containing metal core having a porcelain coating, wherein the porcelain is bonded to the metal core through a continuous layer consisting of nickel aluminide.

6. Process for producing a dental restoration which comprises:
    (a) applying to a surface of a cleaned nickel-containing metal core a coating of a composition that consists of powdered aluminum, a thixotropic agent in an amount of less than 1 weight percent, based on weight of powdered aluminum, and an inert volatile organic liquid carrier;
    (b) baking the coated metal core in a substantially inert atmosphere to a temperature and for a period of time sufficient to form a continuous layer consisting of nickel aluminide on said surface;
    (c) cleaning the coated and based surface; and
    (d) applying porcelain to the baked and cleaned surface and firing.

* * * * *